United States Patent [19]
Weyer

[11] Patent Number: 5,104,485
[45] Date of Patent: Apr. 14, 1992

[54] METHOD OF MEASURING NON-AQUEOUS CONSTITUENTS IN A PULP SLURRY OF A WATER/CELLULOSE MATRIX

[75] Inventor: Lois G. Weyer, Landenberg, Pa.

[73] Assignee: Hercules Incorporated, Wilmington, Del.

[21] Appl. No.: 569,761

[22] Filed: Aug. 21, 1990

Related U.S. Application Data

[63] Continuation of Ser. No. 201,066, May 31, 1988, abandoned.

[51] Int. Cl.$^5$ ................................................. D21C 7/06
[52] U.S. Cl. ...................................... 162/49; 162/198; 250/339; 436/164
[58] Field of Search .......................... 162/49, 62, 198; 250/339; 436/55, 164

[56] References Cited

U.S. PATENT DOCUMENTS

| | | | |
|---|---|---|---|
| 3,228,282 | 1/1966 | Barker | 88/14 |
| 3,405,268 | 10/1968 | Brunton | 250/83.3 |
| 3,551,678 | 12/1970 | Mitchell | 250/83.3 |
| 3,614,445 | 10/1971 | Hill | 250/210 |
| 3,879,607 | 4/1975 | Bjorklund | 250/252 |
| 4,535,239 | 8/1985 | Brighton | 250/339 |
| 4,595,833 | 6/1986 | Sting | 250/339 |
| 4,602,160 | 7/1986 | Mactaggart | 250/341 |
| 4,718,026 | 1/1988 | Long et al. | 364/550 |

FOREIGN PATENT DOCUMENTS

| | | | |
|---|---|---|---|
| WO87/02396 | 4/1987 | PCT Int'l Appl. | 162/198 |
| 2163552 | 2/1986 | United Kingdom . | |

OTHER PUBLICATIONS

Applied Spectroscopy reviews, 21(H2), 1-43(1985) L. G. Weyer, Near-Infrared Spectroscopy of Organic Substances Jour. of Applied Polymer Science, vol. 31, 2417-2431 (1986) L. G. Weyer-Utilizing Zero Crossover Points in Near Infrared Reflectance Analysis.
Applied Spectroscopy vol. 41, No. 5, 1967, 786-790, Weyer et al., Remote Sensing Fiber Optic Probe Nir Spectroscopy Coupled with Chemometric Data Treatment.
Jahrgang, Heft 6, 1987; R. Muller: Selective On-Line Measurement of Fillers.

Primary Examiner—Steve Alvo
Attorney, Agent, or Firm—Connolly & Hutz

[57] ABSTRACT

A method for measuring extremely low concentrations of non-aqueous constituents or chemicals in a water/-matrix, including differentiating between pulp fines and extremely low concentrations of individual chemicals in a water/cellulose matrix such as occur in papermaking. The water/matrix is exposed to the near-infrared spectrum from 1000 to 2500 nm to produce a recorded voltage that is directly proportional to the absorption by the non-aqueous constituent. The amount non-aqueous constituent is determined from stored voltage values of incremental additions of the non-aqueous constituent.

8 Claims, No Drawings

METHOD OF MEASURING NON-AQUEOUS CONSTITUENTS IN A PULP SLURRY OF A WATER/CELLULOSE MATRIX

This application is a continuation of application Ser. No. 07/201,066, filed May 31, 1988, and now abandoned.

INTRODUCTION

This invention relates to measuring extremely low concentrations of chemicals in a water/cellulose matrix. More particularly, this invention relates to differentiating between pulp fines and extremely low concentrations of individual chemicals in a water/cellulose matrix such as occur in papermaking. Still more particularly this invention relates measuring the chemicals retained in the filtrate from passes of the stock slurry, as for example in the filtrate of the first pass in processing a water/cellulose matrix, such as in papermaking.

BACKGROUND OF THE INVENTION

In papermaking an aqueous solution containing cellulose fibers water/pulp matrix is lain on a wire screen which intraps cellulose fibers and permits a filtrate to be removed. The efficiency of the papermaking is influenced by the retention of the process. Thus measuring of the concentrations in the filtrate reports the action in the papermaking pass. Stated otherwise, the concentration of chemicals in the filtrate reflects what is retained on the wire screen. Chemicals as used herein refers to chemical elements, compounds and compositions.

It is known that the overall retention on the wire screen is directly related to the efficiency of the paper making process. For that reason monitoring of the filtrate is an effective means for establishing the nature of the activity in the papermaking procedure. However, available procedures for investigating the filtrates do not provide adequate information about the chemical constituents in the filler of the filtrate from the aqueous slurry. The filtrate contains a low concentration of fine particle material with chemical constituents in a very low concentration.

Present methods are incapable of readily measuring the low concentrations of the individual chemicals in the filtrate by light reflection. Previous methods have not been able to differentiate between very low concentrations of chemicals and the paper fines in a filtrate of a papermaking slurry.

SUMMARY OF THE INVENTION

It is an object of the present invention to provide quantitative measurement of individual chemicals in the filtrate a water/cellulose matrix in papermaking.

A further object is a differentiation among the individual chemicals in a paper-making filtrate and among the pulp fines and chemicals.

It is an object of this invention to provide an analytical means of determining the concentration of chemicals in the filtrate of an aqueous slurry.

A still further object is to employ a mathematical model that provides an identification of chemicals of very low concentration in a slurry containing pulp fines.

Paper chemicals as referred to herein include but are not limited to optical brighteners, sizes and wet and dry strength resins.

In general, this invention provides a method of analyzing and quantitatively measuring individual chemicals in a filtrate of a water/cellulose matrix by scanning the near infrared spectrum with an instrumental system in which radiation from a near infrared instrument is applied to a sample subject and data from the scanning of the near infrared spectrum is collected by detectors. A Pacific Scientific Model 6250 spectrophotometer is suitable.

The data of the infrared spectra obtained by the scanning are stored. The scanning of the infrared spectrum obtains characteristic measurement of the sample subject in data in the form of conversion to voltages which are proportionate and detectable. These measurements recorded are determined by the detection obtained with the spectrometer when scanning in the infrared spectrum.

Information on the identity of the chemicals in a water-cellulose matrix is obtained by scanning by using the radiation of the sample matrix with the spectrometer in the near infrared spectrum. The compositional information is extracted by mathematical treatment utilizing derivatives and multiple linear regressions or other mathematical treatment. By conducting a succession of scans of near infrared spectrum related to a sample subject consisting of a dilute water/cellulose matrix a calibration equation for a specific constituent in the matrix has been obtained.

The data observed in the detector is transmitted to a computer. The computer takes the signals and provides analysis of the slurry from that data.

Near-infrared spectra of the radiation according to the present invention are in a region composed of 1000 nm to 2500 nm, using nanometers as the wavelength unit. The measurement is in absorption and the log (1/reflectance) refers to absorption so that the higher the value the more absorption. The absorption in return relates to the presence of a chemical.

In the present invention the mathematical treatment can be in accordance with the description of wavelength selection methods for data analysis described in *Near-Infrared Technology* edited by Phil Williams and Karl Norris, American Assoc. of Cereal Chemists, Inc. (1987).

By the procedure it has been found that by near-infrared radiation it is possible to determine the levels of low concentrations of an individual chemical in a slurry filtrate in a paper making process.

For example, a succession of scans is conducted with incremental additions of the constituent clay. From the recording of the signals obtained in the near infrared spectra with the recording of the increments of clay a calibration equation for clay in the dilute water/cellulose matrix is obtained.

It has been found that by derivatives and linear regression it is possible to find from the values obtained in the NIR radiation by scanning of the near infrared spectrum with the system in which radiation is applied to a slurry to determine the presence and concentration of the chemicals in the matrix, for establishing a differentiation between the fines and the chemicals in the slurry and in turn establish the amount of chemical retained in a filtrate during papermaking.

An equation has been generated by conducting multiple linear regressions using the data of the weight of clay increments in a succession of slurries and spectral readings from the scanning with the spectrometer. An equation is developed for the constituent, for example, clay.

The data on absorption of the NIR radiation is analyzed by a computer using the mathematical treatment referred to in Near-Infrared Technology, supra to determine the concentration. This radiation signal is stored in the computer and subsequently converted to the percent concentration using an equation of the form:

$$\% = A + B \log 1/R\lambda_1 + C \log 1/R\lambda_2$$

where
A = intercept
B = coefficient of the first term
C = coefficient of the second term
$R\lambda_1 32$ reflectance at wavelength #1 and
$R\lambda_2$ = reflectance at wavelength #2

The NIR technique for analytical measurement is basically a semi-empirical method, the applicability of which requires calibration on the basis of measurements followed by data processing. The investigations are carried on with near infrared spectrometers.

Reference to a procedure involving NIR radiation includes the Near Infrared Reflective method and the Near Infrared Transmittance method.

The purpose of the described technique is to detect and predict the chemical variables in the filtrate from a water/cellulose matrix in papermaking from the spectrophotometric measurements using NIR illumination, either reflectance or transmittance. However, a mathematical relationship for converting the NIR measurements to the desired quantity (the prediction equation) has to be established. As pointed out above, this can be accomplished by a mathematical treatment involving derivatives and linear regression. Suitable techniques are shown in Near Infrared Technoloty supra and in *Calibration of NIR Data by Bilinear Modelling Near Infrared Diffuse Reflectance/Transmittance Spectroscopy*, edited by Hollo, Kaffka and Gonczy, Academy Kiado, Budapest, 1987, pp. 87–95.

DESCRIPTION OF THE INVENTION

To determine the presence of pulp fines and percentage of chemicals in a filtrate, a system was prepared comprised of a transparent container in juxtaposition with a near infrared reflectance instrument which emits a NIR radiation signal directed to impinge on the transparent container and be reflected by the contents. The reflected signal beams were received on suitably arranged detectors of a spectrophotometer.

The contents of the container was aqueous slurry with low concentrations of chemicals and pulp fines, such as occur in a water/cellulose matrix. The near infrared signal beam of the reflectance instrument acted upon the low concentration of chemicals in the slurry and collected on the detectors of the instrument to produce in the instrument a voltage which is directly proportional to the absorption by chemicals in the container. The reflected beam impinges on the slurry and then the instrumenal system scans across the NIR spectrum from 1000 nm to over 2500.

The reflectance of the radiation, as radiation is applied from a near infrared instrument to the slurry and the near infrared spectrum is scanned with an instrumental system and the individual chemicals are measured by the radiation as received by the detector is observed by the computer in the spectrometer. This reflectance signal is stored in the computer and subsequently converted by calculations to the concentration of the chemical in the slurry.

EXAMPLE 1

In an example of the present invention an equation was generated for determining the presence of a very low concentration of clay in a slurry. By using the weight data and the spectral responses, by linear regression the prediction equation set forth above was formulated. A low concentration of clay was provided in a slurry of paper fines and a low concentration of clay. A reading was taken by scanning with near infrared spectra radiation to obtain data on the voltages in the spectrometer which relate to the absorbed spectral radiation resulting from directing of radiation upon the slurry and the reflectance scanning of the infrared spectrum related to the slurry. The slurry scanning was repeated several times and the scans averaged to reduce noise in the data. The reflectance scanning was repeated a number of times with modified slurries each containing an addition of clay so as to provide in each a small incremental change in the concentration of clay in the successive slurries upon which the radiation is directed and absorbed and from which radiation is reflected.

Thus, there was provided slurries containing clay in a very low concentration. Next a near infrared reflectance radiation was directed on said slurries, which reflected signal scanned the near infrared spectrum from 1000 nm to 2500 nm, producing a recordable spectrum reading with said reflected signal, followed by providing a series of near infrared spectrum readings with a succession of slurries of varying concentration. Then computer calculations were performed from the data obtained from the incremental slurries and by linear regressions of the weight data combined with the spectral readings obtained with the compositional values of the clay, a characateristic equation for the clay was obtained.

The equation generated for clay was $-0.006 - 59.243 \log 1/\text{Reflectance}$ at $1370 \text{ nm} + 34.857 \log 1/\text{Reflectance}$ at 1552 of the first derivative near infrared spectrum, obtained with a smoothing of 10 nm. The correlation coefficient of this equation was 0.994 and the standard error of calibration was 0.009 weight percent absolute. Clay was determined at the 0.25 weight percent level in aqueous slurry.

While in the above example, the radiation detected the absorption by reflectance, it will be understood that it is within the scope of this invention to seek the absorbance by a technique of transmittance of the NIR radiation.

EXAMPLE 2

An equation was generated for determining the presence of a very low concentration of water, pulp, clay and titanium dioxide. By using the weight data and the spectral response by linear regression the prediction equation was formulated.

A low concentration of calcium carbonate was provided in an aqueous slurry that contained paper fines, clay and titanium dioxide, also in low concentrations. A reading was taken by scanning with near infrared radiation to obtain data on voltages in the spectrometer which relate to the absorbed spectral radiation resulting from the scanning of the slurry with the radiation. The slurry scanning was repeated and the scans averaged to reduce the noise in the data. This reflectance scanning was repeated with modified slurries each containing an addition of calcium carbonate so as to provide in each a small incremental change in the concentration of calcium carbonate in the successive slurries upon which the radiation is directed and absorbed and from which the radiation is reflected. Thus there was provided a slurry containing calcium carbonate in a very low concentration. Next near infrared reflectance radiation was directed on said slurry, which reflected signal scanned the near infrared spectrum from 1000 nm to 2500 nm, producing a recordable spectrum reading with said reflected signal, followed by providing a series of near infrared spectrum readings with a succession of slurries of varying composition of the calcium carbonate in the slurry.

As illustrated in the following table, in which for the calcium carbonate, pulp, clay and titanium dioxide the data set is shown and the calcium carbonate column shows the grams added to each successive scanned near infrared spectrum related to a slurry.

TABLE

| Sample # | CaCO$_3$ | Clay | TiO$_2$ | Pulp |
|---|---|---|---|---|
| 1 | 0.0071 | 0.007 | | |
| 2 | 0.0072 | | 0.0008 | 0.050 |
| 3 | 0.0071 | | | |
| 4 | 0.0070 | 0.007 | | 0.05 |
| 5 | 0.0071 | 0.007 | 0.001 | |
| 6 | 0.0070 | | | 0.05 |
| 7 | 0.0072 | | 0.0008 | |
| 8 | 0.0071 | 0.007 | | 0.05 |
| 9 | 0.0070 | | | |
| 10 | 0.0071 | 0.007 | | 0.05 |
| 11 | 0.0070 | | 0.001 | |
| 12 | 0.0071 | | | |
| 13 | 0.0074 | 0.007 | | |
| 14 | 0.0072 | 0.007 | | 0.05 |
| 15 | 0.0076 | | | |
| 16 | 0.0071 | 0.007 | 0.001 | |
| 17 | 0.0072 | 0 | | |
| 18 | 0.0070 | 0.007 | | 0.05 |
| 19 | 0.0071 | | 0.001 | 0.05 |
| 20 | 0.0073 | | | 0.050 |
| 21 | 0.0070 | 0.007 | | |
| 22 | 0.0077 | 0.007 | | 0.05 |
| 23 | 0.0070 | | 0.001 | |
| 24 | 0.0068 | 0.007 | | |
| 25 | 0.0071 | 0.007 | 0.001 | |
| 26 | 0.0070 | | | 0.05 |

Then computer calculatons were performed from the data obtained from the incremental slurries and by linear regressions of the weight data combined with the spectral readings obtained with the compositional values of the clay, a characteristic equation for the calcium carbonate was obtained.

The equation was $-0.009 + 5.215 \log 1/\text{Reflectance}$ at 1414 nm $-0.940 \log 1/\text{Reflectance}$ at 2414 nm of the second derivative near infrared spectrium, obtained with a smoothing of 10 nm. The correlation coefficient of this equation was 0.999 and the standard error of calibration was 0.003 weight percent absolute. Calcium carbonate was determined at the 0.25 weight percent level. The experimental conditions were the same as in Example 1.

EXAMPLE 3

By the procedures described above in Examples 1 and 2, an equation was generated from a set of slurries for calibration the same as in Example 2 except that 0.0014 g. to 0.0020 gram increments of titanium dioxide were used for a range of 0.0019 to 0.038 grams in 75 grams of water.

A calibration set of thirty one samples was regressed. A two wave length calibration used 1380 nm and 2260 nm, and the resulting equation was $0.144 - 95.419 \log 1/\text{Reflectance}$ at 1380 nm $+ 24.909 \log 1/\text{Reflectance}$ at 2260 nm of the second derivative spectrum, obtained with a smoothing of 10 nm. The correlation coefficient of this equation was 0.998 and the standard error of calibration 0.0007 weight percent level. The experimental conditions were the same as in Example 1.

This invention provides a method and means for monitoring and controlling the chemicals in a process using a slurry such as papermaking. By contemporaneous evaluation of a filtrate in a papermaking process by scanning with infrared radiation and detecting, identifying and reporting on the status and conditions of chemicals from the data from the filtrate it is possible to monitor the operation, even with the very low concentration of the chemicals in the filtrate and the presence of paper fines.

If the data contains an abnormality, such as an increase in the filtrate in the concentration of clay, calcium carbonate or titanium dioxide, the processing can be appropriately controlled, or corrective action taken.

Various modes of monitoring and controlling are effective. The calculated percentages resulting from application of the equations to the spectra of process streams may be displayed on a CRT screen. Or the monitored data may be gathered and stored in memory for later print-out and display. Or the data may be immediately printed out.

This invention can provide a software performance analysis in which analyzing the data from the scanning of the spectra enables identification of conditions in an operation, such as papermaking, and results in a printing of data from which an operator can obtain information for control and modification of the operation.

What is claimed is:

1. A method of measuring in a filtrate from a pulp slurry of a water/celluose matrix of at least one non-aqueous constituent wherein the filtrate consists of 99% and a total amount of non-aqueous constituents of not more than about 1% by weight
    the steps comprising
    preparing a dilute aqueous dispersion of one or more non-aqueous constituents comprised of at least about 99% by weight of water and not more than about 1% of nonaqueous constituent,
    exposing said dispersion to radiation from a spectrometer across the near-infrared spectrum from 1000 to 2500 nm to produce a recorded voltage that is directly proportional to the absorption by the non-aqueous constituent in the dispersion,
    repeating said exposing to radiation of said dispersion after each of successive recorded incremental additions of non-aqueous constituent and obtaining a succession of recorded voltge levels each a corresponding to the respective recorded successive concentrations of said non-aqueous constitutent to provide in said dilute aqueous dispersion non-auqoue constituents in a concentration of not more than about 1% of said dispersion
    storing the recorded concentrations and corresponding voltage data for the non-aqueous constituent in a computer,
    analysing said recorded concentration and corresponding voltage data for the non-aqueous constituents in the computer, subsequently exposing a filtrate from a pulp slurry of a water/cellulose matrix comprising of about 99% water and not more than about 1% of one or more non-aqueous constituents to the same near-infrared radiation and producing a recorded voltage, storing said recorded voltage in said computer and establishing the amount of the non-aqueous constituency in the filtrate, the non-aqueous constituency in the filtrate being detectable so as to measure the amount of the non-aqueous constituent or constituents in said filtrate.

2. The method of claim 1 in which the additional constituent is a paper chemical.

3. The method of claim 1 in which the additional constituent is clay.

4. The method of claim 1 in which the additional constituent is calcium carbonate.

5. The method of claim 1 in which the additional constituent is titanium dioxide.

6. A method of differentiating in a filtrate from a pulp slurry of a water/cellulose matrix between fines and at least one other non-aqueous constituent wherein the filtrate consists of 99% water and a total amount of non-aqueous constituent of not more than about 1% by weight the steps comprising preparing a dilute aqueous dispersion of fines and one or more additional non-aqueous constituents in an amount of less than 1% by weight of the dispersion exposing said dispersion to radiation from spectrometer across the near-infrared spectrum from 1000 to 2500 nm to produce a recorded voltage that is directly proportional to the absorption by the non-aqueous constituent in the dispersion, repeating said exposing to radiation of said dispersion after each of successive recorded incremental additions consisting of fines and at least one additional non-aqueous constituent and obtaining a succession of recorded voltage levels each corresponding to respective recorded successive concentrations of fines and an additional non-aqueous constituent to provide in said dilute aqueous dispersion, non-aqueous constituents in a concentration of not more than about 1% by weight of said dispersion storing the recorded concentrations and corresponding voltage data for the non-aqueous constituents in a computer, analyzing said recorded concentration and corresponding voltage data for the non-aqueous constituent in the computer, subsequently exposing a filtrate from a pulp slurry of a water/cellulose matrix comprised of about 99% water and not more than about 1% of fines and at least one additional non-aqueous constituent to the same near-infrared radiation and producing a recorded voltage, storing said recorded voltage in said computer and establishing the amount of the fines in the filtrate, fines in an amount of not more than about 1% in the filtrate are detectable so as to differentiate between fines and at least one other non-aqueous constituent.

7. The method as claimed in claim 1 wherein the radiation across the near infrared spectrum is a near infrared reflectance signal which is reflected by said dispersion.

8. The method of claimed in claim 1 wherein the radiation across the near infrared spectrum is a near infrared transmittance signal which transmits the same dispersion.

* * * * *